United States Patent
Liao et al.

(10) Patent No.: US 7,700,355 B2
(45) Date of Patent: Apr. 20, 2010

(54) METHODS OF PRODUCING A POROUS MATRIX FOR CULTURING AND RECOVERING CELLS

(75) Inventors: Chun-Jen Liao, Taipei (TW);
Jui-Hsiang Chen, Hsinchu (TW);
Chen-Chi Tsai, Taipei County (TW);
Yung-Chih Wu, Taipei County (TW);
Shu-Fang Chiang, Hsinchu (TW);
Yi-Jung Hsiang, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 535 days.

(21) Appl. No.: 11/030,150

(22) Filed: Jan. 7, 2005

(65) Prior Publication Data
US 2006/0153814 A1    Jul. 13, 2006

(51) Int. Cl.
*C12N 5/00* (2006.01)
*C12N 5/06* (2006.01)
*C12N 5/08* (2006.01)
*C12N 11/10* (2006.01)
*C12N 11/12* (2006.01)
*C12N 1/02* (2006.01)
*C12N 5/02* (2006.01)

(52) U.S. Cl. .................. 435/395; 435/178; 435/179; 435/261; 435/325; 435/403

(58) Field of Classification Search .............. None
See application file for complete search history.

(56) References Cited

U.S. PATENT DOCUMENTS

| 5,073,491 | A |   | 12/1991 | Familletti |
| 5,254,471 | A |   | 10/1993 | Mori et al. |
| 5,266,476 | A |   | 11/1993 | Sussman et al. |
| 5,585,183 | A |   | 12/1996 | Chu |
| 5,723,601 | A |   | 3/1998 | Larsson |
| 5,840,777 | A |   | 11/1998 | Eagles et al. |
| 5,866,155 | A | * | 2/1999 | Laurencin et al. ........... 424/425 |
| 6,436,426 | B1 |   | 8/2002 | Liao et al. |
| 6,673,285 | B2 | * | 1/2004 | Ma .............................. 264/49 |
| 6,730,314 | B2 |   | 5/2004 | Jeschke et al. |
| 6,797,738 | B2 | * | 9/2004 | Harris et al. ................. 521/149 |

OTHER PUBLICATIONS

Chung et al., "Preparation of alginate/galactosylated chitosan scaffold for hepatocyte attachment", Biomaterials, vol. 23 (2002), pp. 2827-2834.

* cited by examiner

*Primary Examiner*—David M Naff
(74) *Attorney, Agent, or Firm*—Birch, Stewart, Kolasch & Birch, LLP

(57) ABSTRACT

A porous matrix, preparation thereof, and methods of using the same. The porous matrix of calcium alginate is prepared using a plurality of particles containing a multivalent cation, admixing the particles with ionic cross-linked polysaccharides and water to form a mixture, introducing a cross linker to solidify the mixture, dissolving the particles of the mixture in an acid to form a porous structure, and neutralizing and cross-linking the porous structure.

19 Claims, 13 Drawing Sheets

METHODS OF PRODUCING A POROUS MATRIX FOR CULTURING AND RECOVERING CELLS

BACKGROUND OF THE INVENTION

1. Field of the Invention

The invention relates to a porous matrix, the preparation thereof, and methods of using the same.

2. Brief Discussion of the Related Art

Mass cell production is important in tissue engineering, protein drug production, and cell therapy. The conventional mass cell production technology includes static flat culturing and dynamic bioreactor culturing. Static flat culturing is appropriate for small-scale trials such as $10^6$-$10^8$ cells cultured in laboratory or factory. To compensate for the limited surface of the culture plate, large-scale culture requires numerous culture plates, however, manual operation such as seeding cells, changing media, passaging or harvesting cells increases labor burden and the risk of contamination. It is, therefore, not economical for mass production of animal cells.

Bioreactors provide sufficient metabolic exchanges and are popular in mass production of animal cells. Bioreactors for adherent cells can be two- or three-dimensional. The former provides solid micro-beads for cells to attach to in a two-dimensional manner and also evenly distributed nutrients. Cells proliferated in this system may, however, be dedifferentiated by shear stress and friction produced by the stirring in the bioreactor, harmful to the cells. The later has porous matrices for cells to attach to in a three-dimensional manner and provides a larger space for cell growth and less shear stress, however, harvesting cells can be impeded. The proliferated cells may form an aggregate within the matrix and cannot be simply harvested by regular digesting enzyme. The longer digestion time required, however, may greatly reduce the recovery rate.

Matrices for adherent cells include natural materials such as collagen, gelatin, chitosan, or artificial material such as polyglycolide acid (PGA), polylactide acid (PLA), poly(glycolide co-lactide) acid (PLGA). These materials provide a biocompatible, biodegradable, 3-dimensional scaffold for cell attachment and proliferation and are designed to be implanted into living subjects with the culturing cells for replacement or repair of injured tissues or organ. Recovery rate is not a major issue for this application.

Materials for the production of protein drugs are not designed to be implanted into living subjects and can be artificial polymers such as polystyrene (PS), polyvinyl chloride (PVC), or polymethyl acrylate resin. For example, U.S. Pat. No. 5,254,471 discloses a carrier for cell culture comprising polyester fibers. The carrier makes it possible for the cells to retain their differentiation and proliferation ability for a long time, however, cell recovery from the carrier can be a problem. U.S. Pat. No. 5,266,476 also discloses a matrix and cultivation system for anchorage-dependent cells. The matrix provides a substantially increased available effective surface area for cell attachment by the use of non-woven or open-pore foams with suitable pore size. This matrix is suitable for cell proliferation and growth, but not appropriate for the recovery of cells.

A new matrix material is alginates, a family of unbranched polysaccharides with properties that vary widely depending on their composition. In the presence of divalent cations such as calcium ion, alginates form a gel, however, gel formation can be reversed by adding ion chelating agents such as EDTA. Recently, alginates have been used to encapsulate a variety of biological materials, including cells. For example, U.S. Pat. No. 5,585,183 discloses a method for preparing liquid-core microcapsules for cell cultures, using a hardening solution containing $CaCl_2$ and polyethylenimine to harden alginate gel-core beads before coating them with polylysine solution and dissolving calcium ion with sodium citrate. The liquid-core microcapsules solve the problem of mechanical disruption, but the cultured cells cannot be released easily. Further, the growing space of the liquid-core microcapsules is limited.

U.S. Pat. No. 6,730,314 discloses a method for the production of chodrocytes. The method comprises encapsulating the chondrocytes in alginate beads, cultivating the encapsulated chondrocytes under a low oxygen pressure, and isolating the encapsulated chondrocytes from the alginate beads by a chelating agent for cartilage implantation. U.S. Pat. No. 5,073,491 discloses a method for cells in a bioreactor having a growth chamber for receiving the cells. The method comprises combining cells with gelatin particles to form a cell-gelatin particle suspension, mixing alginate with the cell-gelatin particles to form an alginate-cell-gelatin suspension, polymerizing the alginate to form alginate beads having the cells and gelatin particles entrapped therein, and heating the alginate beads to dissolve the gelatin particles and thereby form cavities within the alginate beads. The cavities contain the cells to be grown. In these methods, alginates are limited to encapsulating cells and the cell recovery is low or even not mentioned.

Also related to alginates are U.S. Pat. No. 5,840,777 and U.S. Pat. No. 5,723,601. The patents disclose methods of producing polysaccharide foams containing alginate by freezing and drying technology. This technology is time- and energy-consuming and cannot be used in large scale. In addition, porosity, pore size, and even cross-linking cannot be controlled. The application of cell culture is not well addressed in the two patents.

High density culture of anchorage dependent cells in carrier systems, especially the alginate system, however, is still restricted in some ways, therefore, a cell matrix providing excellent growth environment and high recovery rate is still required.

SUMMARY OF THE INVENTION

Accordingly, an embodiment of the invention provides a method for producing a porous matrix, comprising providing a plurality of particles containing a multivalent cation, admixing the particles with ionic cross-linked polysaccharides and water to form a mixture, introducing a cross linker to solidify the mixture, dissolving the particles of the mixture in an acid to form a porous structure, and neutralizing and cross-linking the porous structure to obtain the porous matrix.

Also provided is a porous matrix prepared by the method described above.

Further provided is a method of culturing and recovering cells from the porous matrix prepared by the process described. The method comprises seeding cells into a solution comprising the porous matrix, cultivating the cells, dissolving the cell matrix in an ion chelating agent, and collecting the cells.

Further scope of the applicability of the present invention will become apparent from the detailed description given hereinafter However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the following detailed description and the accompanying drawings, which are given by way of illustration only, and thus are not limitative of the present invention, and in which:

FIG. 6A-6C are photographs showing the cell matrices of embodiments of the invention, in which FIG. 6A shows the cell matrices partially dissolved after adding 40 ml of 100 mM EDTA, FIG. 6B shows the cell matrices totally dissolved after 10 min reaction, FIG. 6C shows the harvested HepG2/C3A cells after centrifugation.

FIG. 7A: 100×; FIG. 7B: 200×.

FIG. 8A: small cell mass (50 μm); FIG. 8B: large cell mass (150 μm).

FIG. 11A~11C are photographs showing L929 cells cultured in the cell matrices of embodiments of the invention, in which FIG. 11A shows L929 cells cultured in the cell matrices for one week, FIG. 11B shows the cell matrices partially dissolved after adding 40 ml of 100 mM EDTA, and FIG. 11C shows the harvested L929 cells after centrifugation.

FIG. 12A: 100×; FIG. 12B: 200×.

DETAILED DESCRIPTION OF THE PREFERRED EMBODIMENTS

Figure 1:
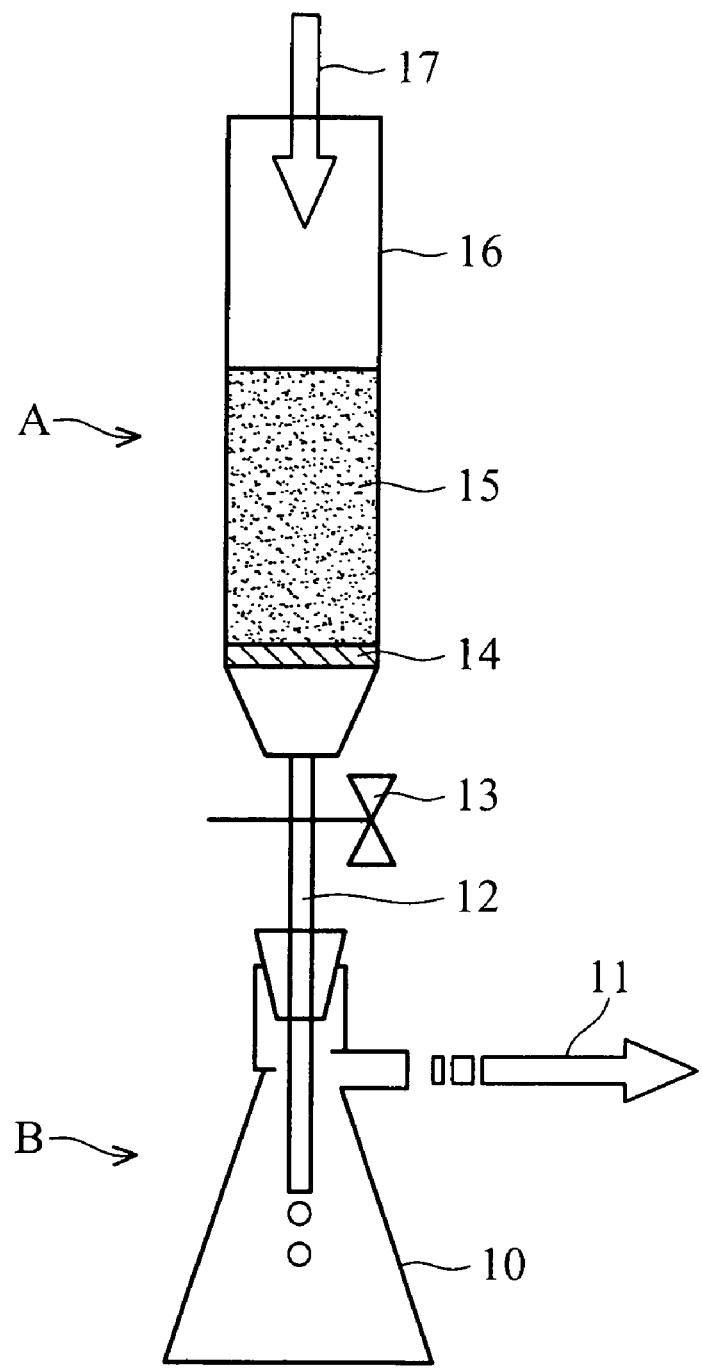
FIG. 1 illustrates a filtration system for the preparation of the porous matrix in an embodiment of the invention.

A porous matrix, the preparation thereof, and the method using the same are provided.

An embodiment of a method of producing the porous matrix comprises provides a plurality of particles containing a multivalent, admixing the particles with ionic cross-linked polysaccharides and water to form a mixture, introducing a cross linker to solidify the mixture, dissolving the particles in an acid to form a porous structure, and neutralizing and cross-linking the porous structure to obtain the porous matrix. The embodiment of the method can further comprise a step of washing the porous matrix after the neutralization and cross-linking step.

The ionic cross-linked polysaccharides can be, but are not limited to alginate, N,O-carboxymethyl chitosan, or carboxymethyl cellulose, preferably alginate.

The particles may be hydroxyl-apatite (HAP), tricalcium phosphate (TCP), tetracalcium phosphate ($Ca_4P_2O_9$), $CaHPO_4$, $CaHPO_4 \cdot 2H_2O$, octacalcium phosphate (OCP), $Ca_2P_2O_7$, calcium carbonate, calcium sulfate, magnesium carbonate, magnesium sulfate, or calcium phosphate, preferably calcium phosphate. In addition, the particle is between 50~2000 μm in diameter.

The cross-linker may also be, but is not limited to, calcium chloride, calcium sulfate ($CaSO_4$), calcium carbonate ($CaCO_3$), strontium chloride ($SrCl_2$), strontium sulfate ($SrSO_4$), strontium carbonate ($SrCO_3$), barium chloride ($BaCl_2$), barium sulfate ($BaSO_4$), or barium carbonate ($BaCO_3$), preferably calcium chloride.

The acid can be hydrogen chloride (HCl), hypochlorous acid (HClO), phosphinic acid ($H[PH_2O_2]$), phosphonic acid ($H_2PHO_3$), phosphoric acid ($H_3PO_4$), carbonic acid ($HCO_3$), acetic acid ($CH_3COOH$), or formic acid (HCOOH), preferably hydrogen chloride.

The neutralization and cross-linking step can be performed by calcium hydroxide, strontium hydroxide ($Sr(OH)_2$), or barium hydroxide ($Ba(OH)_2$), preferably by calcium hydroxide.

In one embodiment, the method for producing a porous matrix employs the reversible property of alginate gel formation to produce a three-dimensional porous matrix. Particles containing a multivalent cation such as calcium phosphate particles can be admixed with alginate such as sodium alginate and water in a mold with negative pressure and the partially dissolved sodium alginates may be linked one another. Addition of negative pressure and introduction of a cross linker such as a calcium chloride solution can then be applied to the mold to partially cross-link and solidify the mixture of sodium alginate, particles, and water. The molded mixture may be immersed in an acid to dissolve the particles from the mixture. During the acid dissolution step, sodium ions of sodium alginate can be replaced by hydrogen ions from the acid. In addition, calcium ions of the particles can be released, resulting in cross-linking between particles and alginates. After the acid dissolution step, the space previously occupied with the particles may be void and the porous structure can be obtained. After rinsed with water, the porous structure can then be neutralized and finally cross-linked with excess of calcium hydroxide. Hydroxide ion of calcium hydroxide may neutralize hydrogen ion in the porous structure. The porous matrix of the invention can then be achieved.

The porous matrix provides large growing space for high density cell culture. The recovery of cells is simple and not harmful to the cells. An ion chelating agent in a concentration familiar to the cells may be applied to the culture and the cell matrix can be completely dissolved. The cells can then be harvested by a simple centrifugation.

Alginate produced by brown seaweeds is a linear, unbranched polysaccharide composed of 1,4-linked β-D-mannuronic acid (M) and α-L-guluronic acid (G). Depending on the source algae, alginates may have different M/G ratio, leading to various conformational preferences and behaviors. Gel formation of alginate is a reversible reaction and can be achieved by adding divalent cations such as calcium ion or dissolved by adding an ion chelating agent such as EDTA.

In addition, alginate is biocompatible, hydrophilic, and biodegradable under normal physiological conditions. These unique properties enable alginate to be utilized as a matrix material in the sustained release application and for implantation and encapsulation of isolated cells. On the other hand, disadvantages of alginate matrix include unstable mechanical properties due to the ion exchange of crosslinked divalent cations with monovalent cations, and lack of specific cell-recognition signals, which enable the anchorage-dependent cells to promote the interaction with the matrix.

Conventional preparation of alginate gel for cell culture usually comprises dissolving sodium alginate in water and adding a solution containing calcium ion such as calcium chloride to exchange the calcium ion and sodium ion. The obtained alginate gel is restricted to microparticles of diameter less than 100 μm or liquid-cell-microparticles since the cross-link of surface may impede inner cross-link reaction. While dialysis may solve the problem, cross-linked gradients and uneven cross-linking are further issues. In addition, the dissolution of this alginate matrix cannot be controlled. In the method disclosed, the prepared cell matrix provides a three-dimensional porous structure with interconnecting pores, and cross-linking is evenly distributed.

Moreover, exchange efficacy of sodium ion to calcium ion can also be an issue. Alginates are usually used for cell encapsulation rather than cell matrix because cells having negatively charged surfaces cannot attach to the negatively charged surface of sodium alginate. Here the addition of multivalent cations such as calcium ion or magnesium ion on the surface of alginate to form calcium alginate or magnesium alginate may facilitate cell attachment.

In an embodiment of a method of culturing and recovering cells from a porous matrix, cells are suspended in a medium to form a cell suspension. The cells are anchorage-dependent and can be animal cells or plant cells. The cell suspension is seeded into a solution comprising the porous matrix and the cells cultured under suitable conditions, such as culturing first in a static flat culturing system and then in a dynamic bioreactor culturing system. When the cells are to be harvested, the cell matrix can be dissolved by an ion chelating agent and the cells collected. The ion chelating agent can include, but is not limited to, EDTA (ethylenediminetetraacetic acid), sodium citrate, or EGTA (ethyleneglycol-bis(2-aminoethylether)-N', N',N',N'-tetraactic acid).

Practical examples are described herein.

EXAMPLES

Example 1

Preparation of Porous Alginate Matrix

In brief, soluble alginate was admixed with calcium phosphate particles to form a mixture. For an even distribution of calcium phosphate, the mixture was placed into a mold as disclosed in U.S. Pat. No. 6,436,426. Calcium ion solution was introduced into the mixture to perform cross linking, and calcium phosphate was dissolved by acid to leave a plurality of voids in the mixture.

The calcium phosphate particles were prepared from a compact bone of a cattle thighbone. The thighbone was heat-treated at 900° C. to remove organic components and decarbonizes to obtain inorganic calcium phosphate. A lump of inorganic calcium phosphate was then pulverized in a disintegrator. The particles were passed through a sieve of 40~60 mesh to obtain calcium phosphate particles between 250~420 μm for the following procedure. The solution used for cross linking was 1% calcium chloride.

Appropriate amounts of deionized water were added to 17.14 g of calcium phosphate particles and the excess water removed by vacuum filtration to final water content of 14.6±3.2%. 0.98 g of sodium alginate powders (low viscosity, Mw: 12000~80000, Sigma Chemical Co.) were admixed with the hydrous calcium phosphate particles and 0.98 g of anhydrous calcium phosphate particles thoroughly to form a mixture of calcium phosphate particles and sodium alginate. The mixture was poured into the device shown in FIG. 1, comprising a filtration unit A and a connected suction unit B and providing pressure difference. The filtration unit A comprises a filtration vessel 16 holding the mixture of sodium alginate powders and calcium phosphate particles 15, a filter film 14, a valve 13 controlling a filtrate flowing in the filtration vessel 16, a filtrate conduit 12 for the filtrate flow, and a filtrate vessel 10 receiving the filtrate.

One percent of calcium chloride solution 17 was added to the mixture in the filtration vessel 16 for cross linking between calcium phosphate and sodium alginate. The Vacuum unit B provided pressure difference for surplus solution, generating cross-linking between the surface of calcium phosphate particles and the partially dissolved sodium alginate. The solidified matrix was removed to a beaker with 0.6N HCl solution. The HCl solution was replaced every day at room temperature. The matrix was stirred in the HCl solution for three days to wash out calcium phosphate particles. The matrix was placed in 1% calcium hydroxide solution for neutralization and solidification. After 1 hour, calcium hydroxide solution in the matrix was washed out by deionized water, and the porous matrix was obtained.

Figure 2:
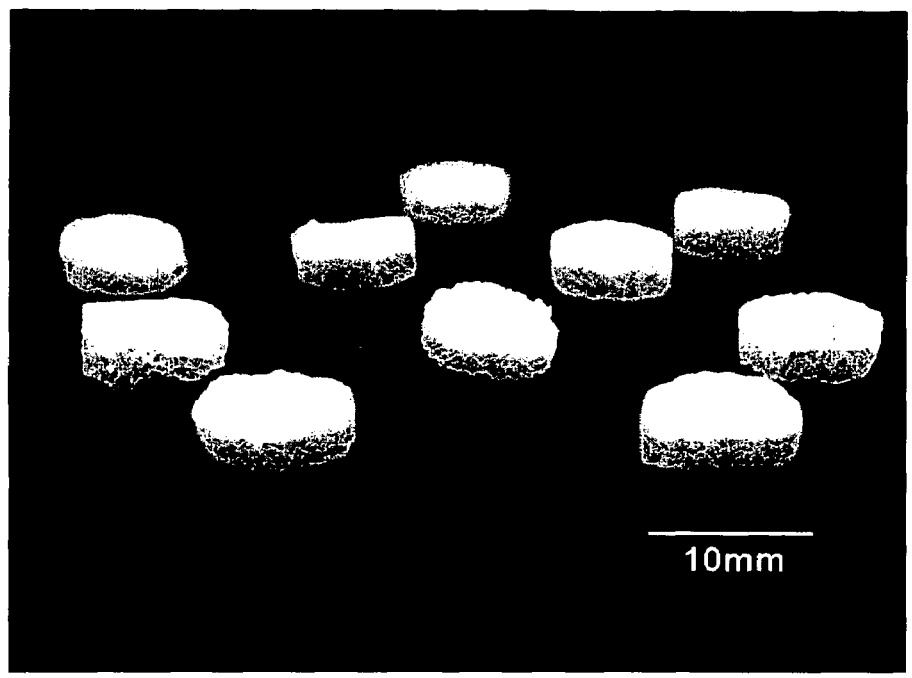
FIG. 2 is a photograph showing the porous cell matrices prepared in embodiments of the invention.

The obtained porous matrix was sliced into round tablets 8 mm in diameter and 3 mm in thickness as shown in FIG. 2. The pore size of the porous matrix was tested according to ASTM D-3576-94 and porosity measured by Optimas Image Analysis Software Version 6.5 (Media Cybermetics, L.P.) The microstructure of the porous matrix was observed under scanning electron microscope, operated at a current of 40 mA.

Figure 3:
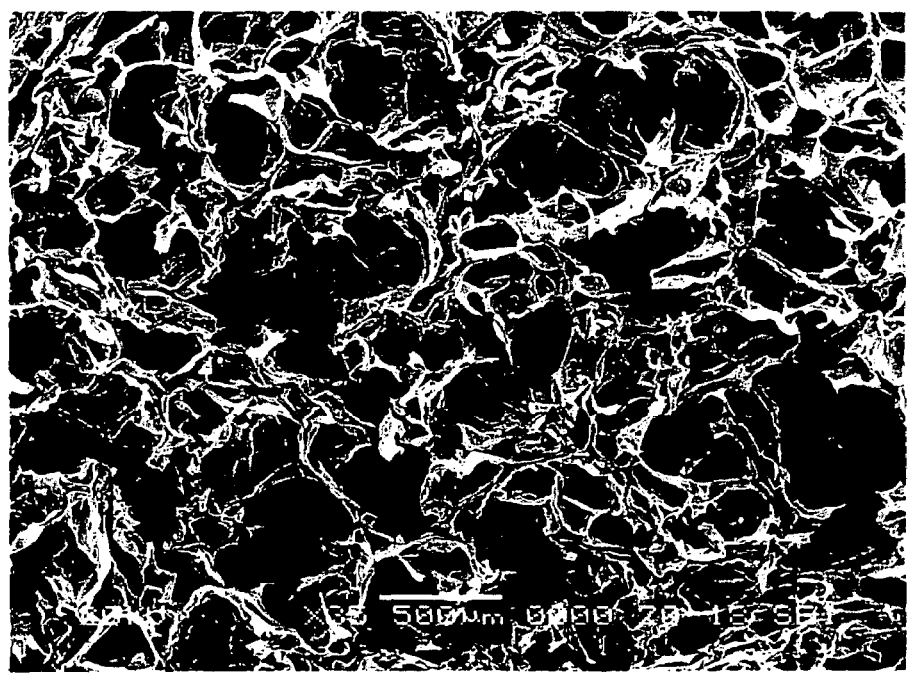
FIG. 3 is a scanning electron microscopic photograph showing the porous structure of the cell matrix in embodiments of the invention.

The results show that the pore size of the porous matrix is 317±153 μm, with porosity is 87.4±5.4%. FIG. 3 is a scanning electron microscopic photograph showing the porous matrix. The porosity distribution of the porous matrix is uniform and the pores interconnected.

Example 2

Culture and Recovery of HepG2/C3A in the Cell Matrix of the Embodiment of the Invention Human hepatoma cell line HepG2/C3A was maintained in MEM supplemented with 10% FBS, 3.7 g/L sodium bicarbonate, and 1% antibiotic-antomyotic at 37° C. in a 5% $CO_2$ incubator. The cells were incubated in a flat dish and passage of the cells was performed with trypsin when the cells were confluent. The cells were counted.

Each $5×10^5$ of HepG2/C3A cells were placed in a 15 ml centrifugation tube. The cells were immersed in 2 ml of DPBS, or 50, 100, or 200 mM of EDTA for 10 or 20 min, respectively. Thirteen ml of medium was added into the cells, the mixture was centrifuged, and the supernatant was discarded. One ml of medium was added to suspend the cells. Twenty λ of cell suspension was mixed with 20λ of trypan blue for cell viability to determine cell tolerance in EDTA solution. The results are listed in Table 1.

TABLE 1 tolerance of HepG2/C3A cells in EDTA solution

| | 10 min | | 20 min | |
|---|---|---|---|---|
| EDTA\time | Cell viability (%) | Death rate (%) | Cell Viability (%) | Death rate (%) |
| DPBS | 92.2 | 0.8 | 98.9 | 1.1 |
| 50 mM EDTA | 97.8 | 2.2 | 98.9 | 1.1 |
| 100 mM EDTA | 99.4 | 0.6 | 95.0 | 5.0 |
| 200 mM EDTA | 74.3 | 25.7 | 63.0 | 37.0 |

As shown in Table 1, Cells immersed in EDTA solution at a concentration below 100 mM for 10 min or even 20 min are alive and intact, however, in EDTA solution at a concentration of 200 mM or higher, part of the cells may be damaged.

To determine the cell matrices suitability for culturing cells, $2 \times 10^6$ of HepG2/C3A cells were suspended in 6 ml of medium and seeded into the prepared porous matrices. The cells were cultured in a static condition for 8 hours to be attached on the matrices and then cultured under a perfusion culturing system for 14 days. After that, the cell matrices were dissolved with 100 mM EDTA and cells were collected for analysis. The dissolution time was measured. Total cell number was measured by DNA quantitative analysis. The cells were digested with 100~200 μg/ml of protease K at 50° C., and DNA of the cells was stained with Hoechst 33342 and measured at 350 nm excitation wavelength and 460 nm emission wavelength. Cell morphology was observed under microscope and scanning electron microscope. In addition, the recovery cells were continuously cultured for 3 days to observe cell viability, cell morphology, cell proliferation, and cell function.

Figure 4:
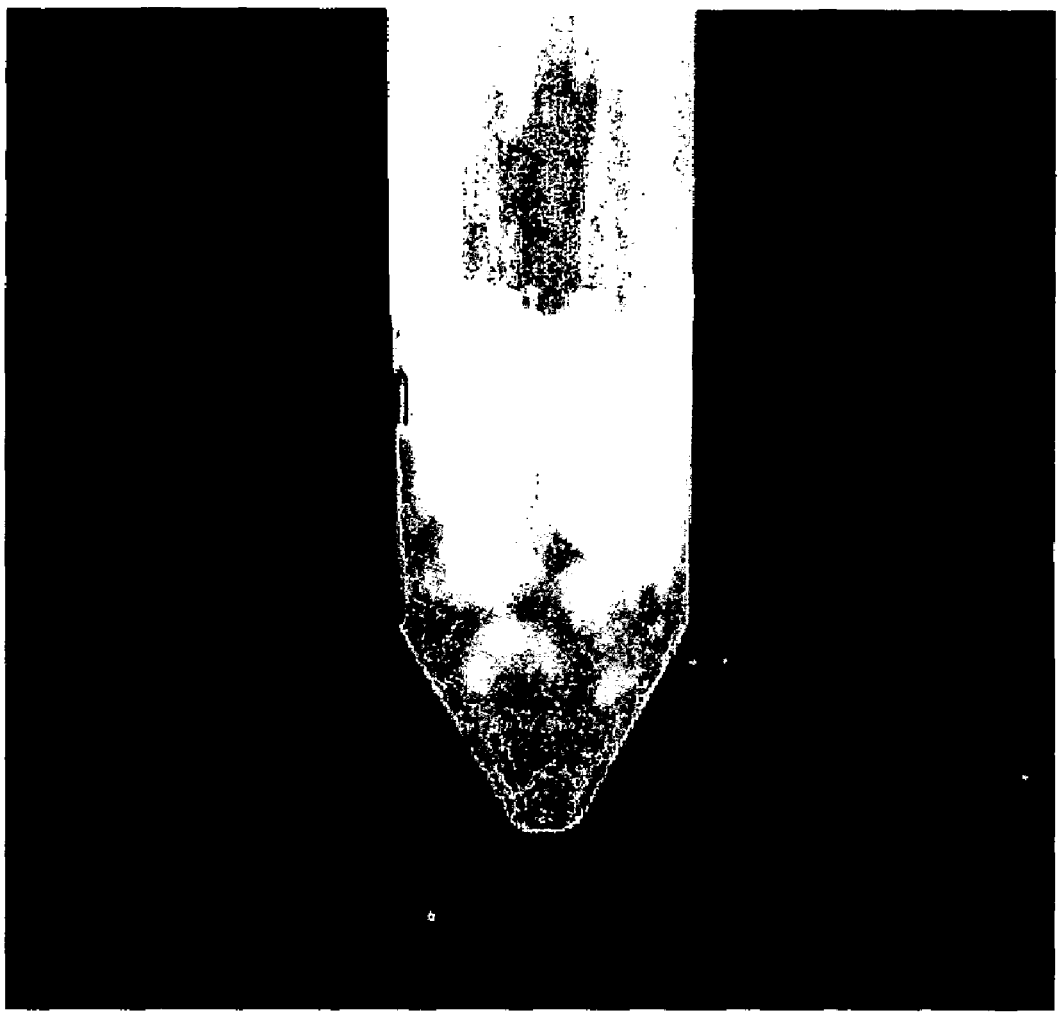
FIG. 4 is a photograph showing the cell matrices of embodiments of the invention after a two-week perfusion culturing.
Figure 5A:
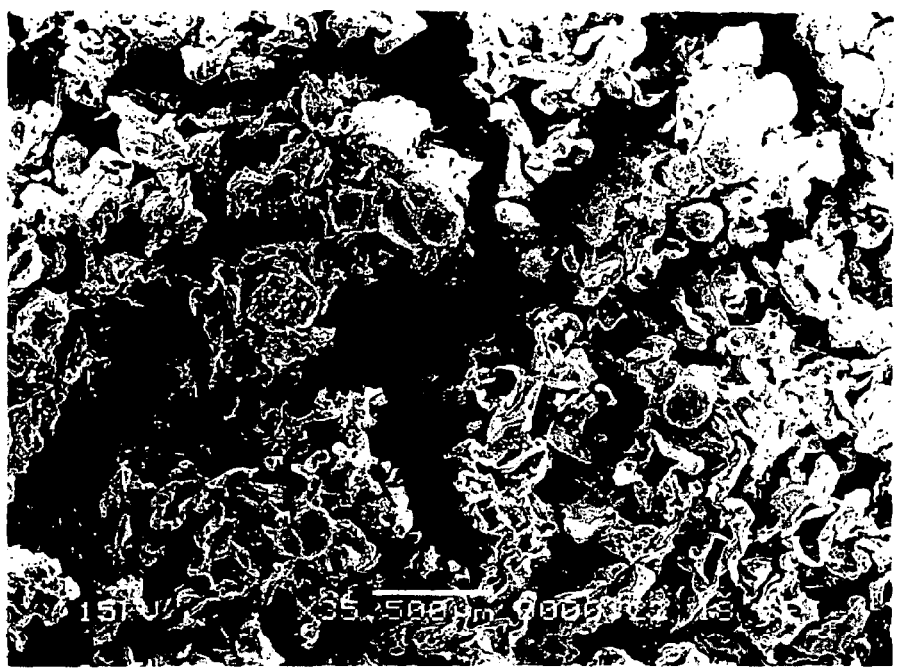
FIGS. 5A and 5B are scanning electron microscopic photographs showing the proliferation of HepG2/C3A cells in the cell matrix of embodiments of the invention.
Figure 5B:
Figure 6C:
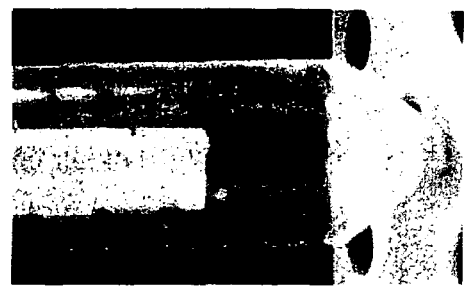
Figure 6B:
Figure 6A:
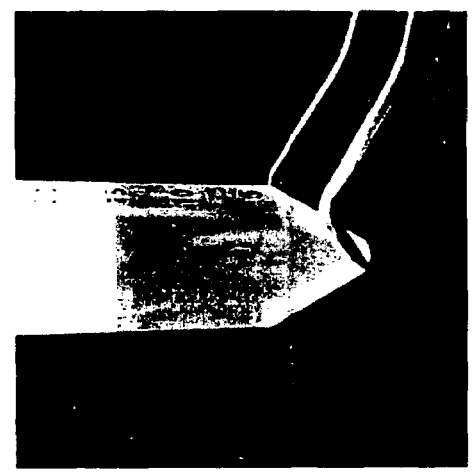
Figure 10A:
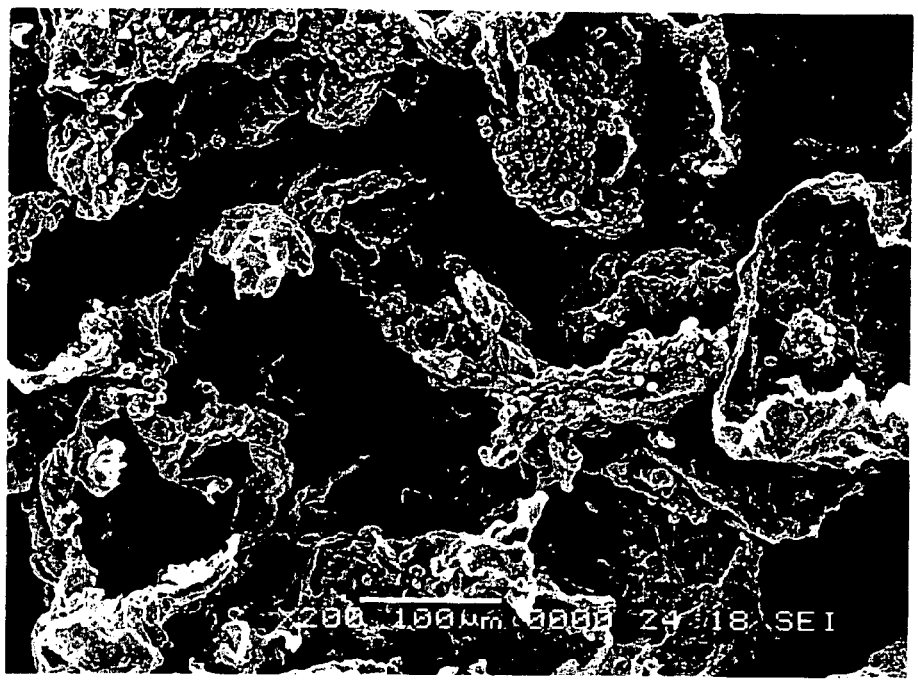
FIGS. 10A and 10B are scanning electron microscopic photographs showing the growth of L929 cells in the cell matrices of embodiments of the invention.
Figure 10B:
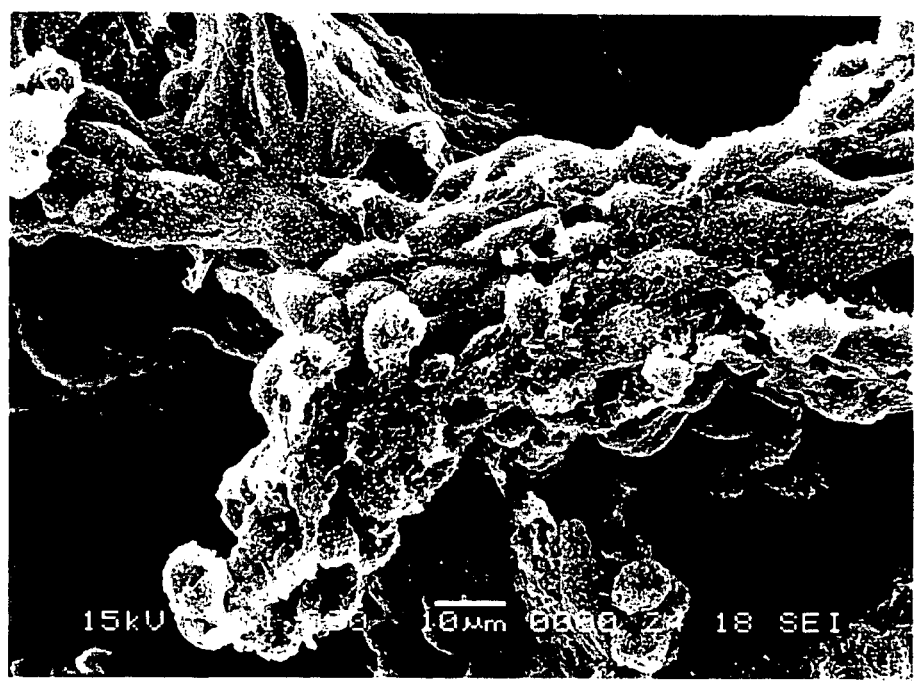

FIG. 4 is a photograph showing the cell matrices after two-week perfusion culturing. The cell matrices are still intact. Scanning electron microscopy results in FIGS. 5A and 5B reveal that HepG2/C3A cells were grown and proliferated in the matrices in a spherical presentation. When the cell matrices were added to 40 ml of 100 mM EDTA for 3 min, they were partially dissolved as shown in FIG. 6A, and 10 min later, the cell matrices were totally dissolved as shown in FIG. 6B. FIG. 6C shows that the cells were precipitated by centrifugation after the cell matrices were dissolved.

Figure 7A:
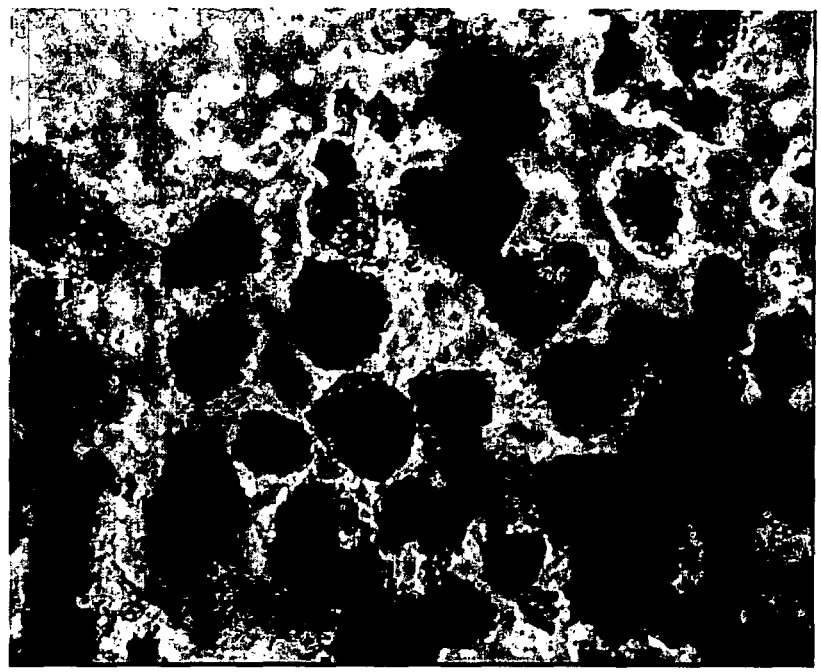
FIGS. 7A and 7B are microscopic photographs showing HepG2/C3A cells harvested from the cell matrix culturing in embodiments of the invention.
Figure 7B:
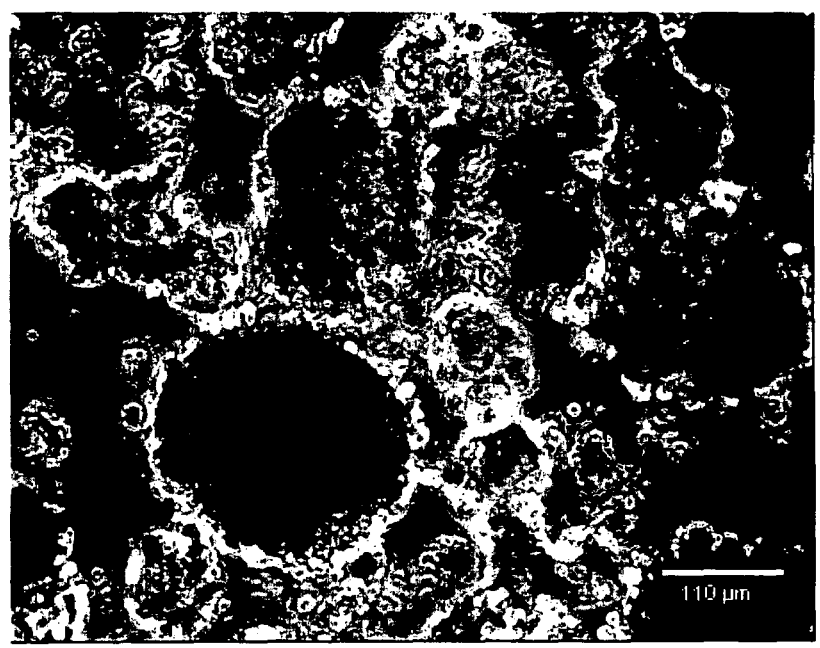

FIGS. 7A and 7B are microscopic photographs showing HepG2/C3A cells harvested from the cell matrix culturing. The cells are mostly in a spherical presentation.

Figure 8A:
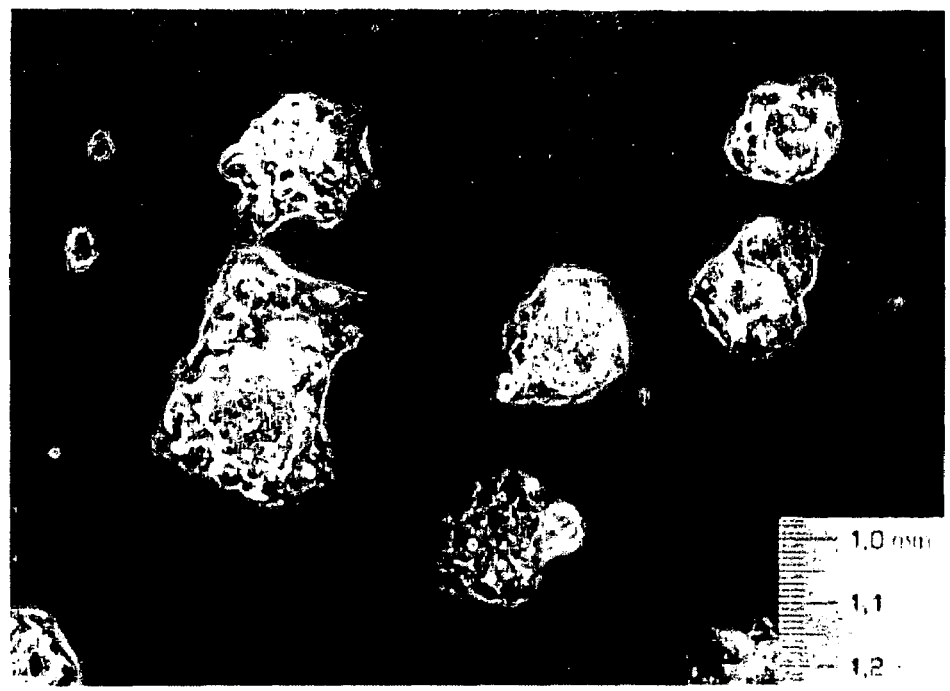
FIGS. 8A and 8B are microscopic photographs showing HepG2/C3A cells cultured for one-day in a flat dish after harvesting from the cell matrices in embodiments of the invention.
Figure 8B:
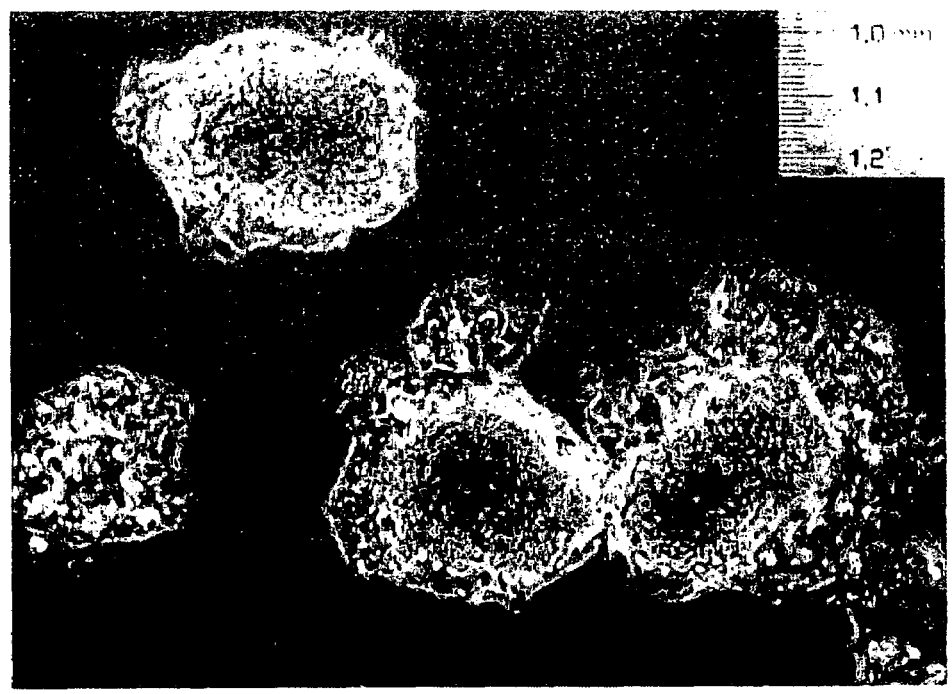
Figure 9:
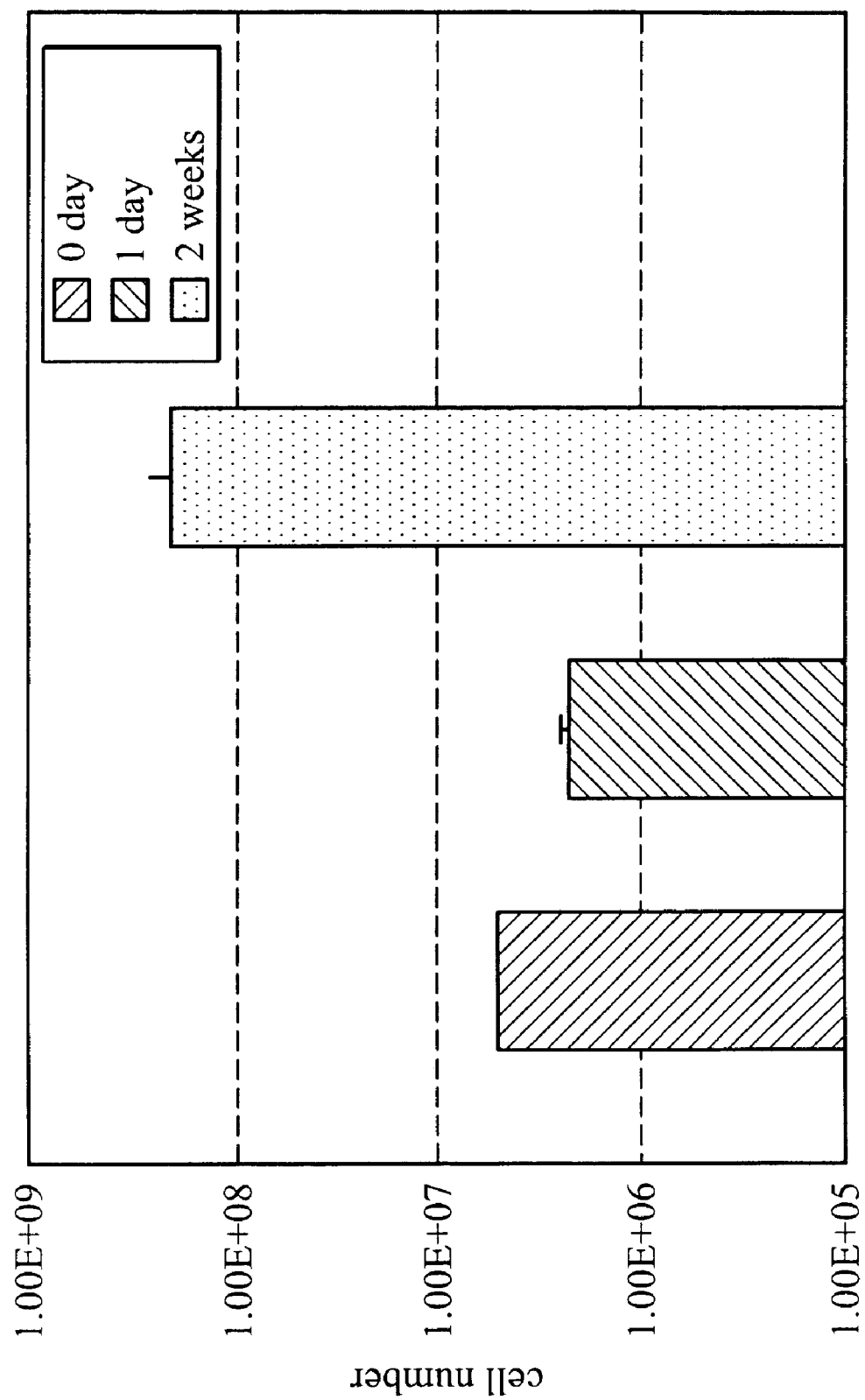
FIG. 9 is a diagram showing HepG2/C3A cell numbers changing at different time points after culturing in the cell matrices of embodiments of the invention.

The observation of the cells cultured for one-day in a flat dish after harvesting from the cell matrices shows that cells in a spherical presentation at different sizes were attached and proliferated normally in FIGS. 8A and 8B. This indicates that the recovery method in the example of the invention does not damage the cells. FIG. 9 is a diagram showing the HepG2/C3A cell number changes at different times after culturing in the cell matrices. The results indicate that the cell matrix of the example of the invention provides sufficient space for cells to grow and proliferate. The proliferation of HepG2/C3A cells cultured for 2 week in the cell matrices is 87 times that of the original seeding cells.

Example 3

Culture and Recovery of L929 Cells

Mice fibroblast cells L929 were maintained in DMEM supplemented with 10% FBS, 3.7 g/L sodium bicarbonate, and 1% antibiotic-antomyotic at 37° C. in a 5% $CO_2$ incubator. The cells were incubated in a flat dish and passage of the cells was performed with trypsin when the cells were confluent. The cells were counted. $10^6$ of L929 cells were suspended with 6 ml medium and seeded into the prepared porous matrices. The cells were cultured in a static condition for 4 hours to be attached on the matrices and then cultured under a perfusion culturing system for 7 days. The cell matrices were dissolved with 100 mM EDTA and cells were collected for analysis.

Dissolution time was measured. Total cell number was measured by DNA quantitative analysis. The cells were digested with 100~200 μg/ml of protease K at 50° C., and DNA of the cells was stained with Hoechst 33342 and measured at 350 nm excitation wavelength and 460 nm emission wavelength. Cell morphology was observed under microscope and scanning electron microscope. In addition, the recovery cells were continuously cultured for 3 days to observe cell viability, cell morphology, cell proliferation, or cell function.

Figure 11A:
Figure 11B:
Figure 11C:
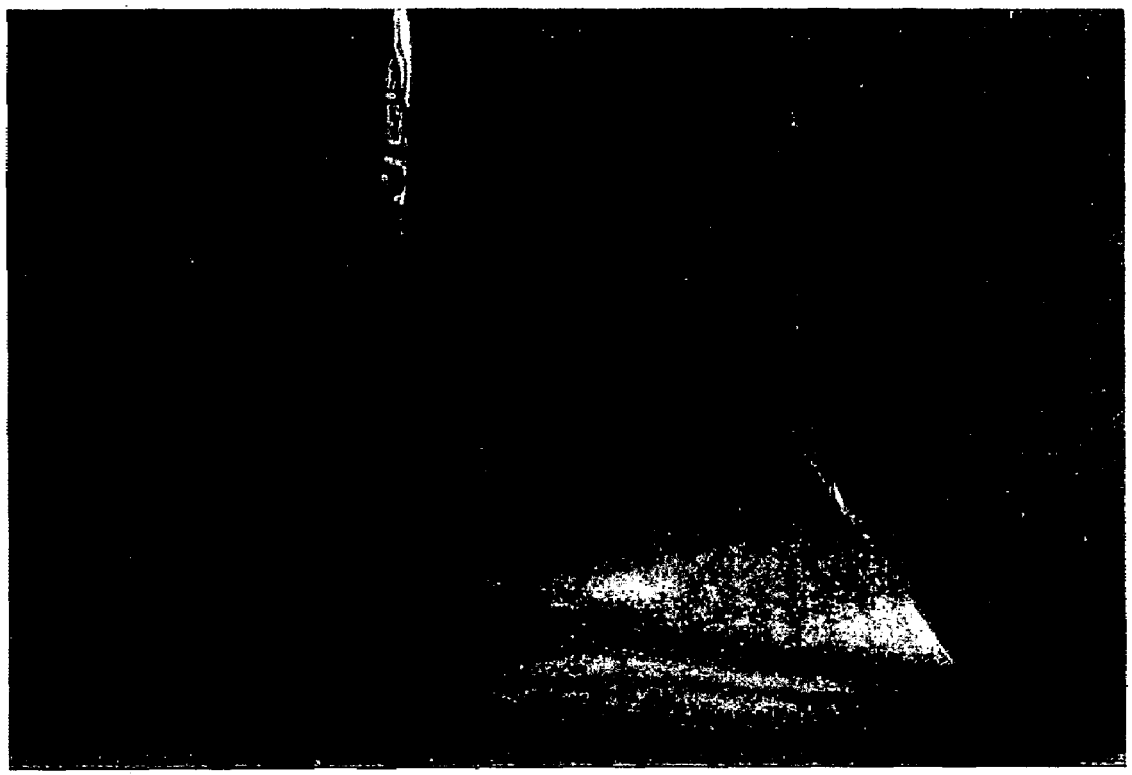

The cell matrices were still intact after one-week perfusion culturing as shown in FIG. 11A. The observation of scanning electron microscope as shown in FIGS. 11A and 11B appears that L929 cells were extensively distributed in the pores of the matrices. When the cell matrices were added with 40 ml of 100 mM EDTA for 3 min, they were partially dissolved as shown in FIG. 11B. FIG. 1 IC shows that the cells were precipitated by centrifugation after the cell matrices were totally dissolved. This indicates that the cells cultured in the cell matrices of the example of the invention can be completely recovered.

Figure 12A:
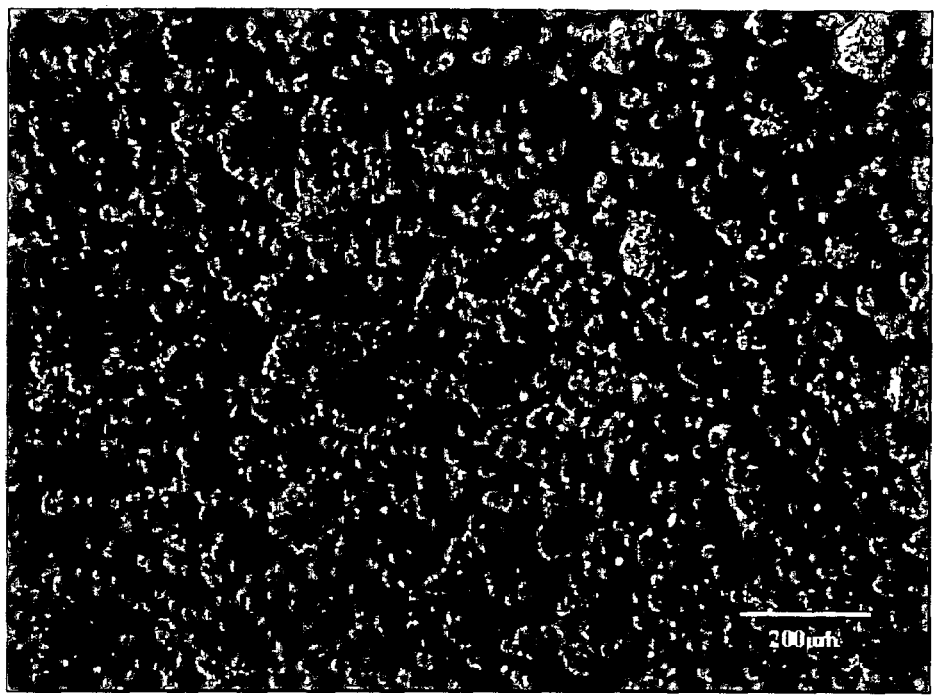
FIGS. 12A and 12B are microscopic photographs showing L929 cells harvested from the cell matrix in embodiments of the invention.
Figure 12B:
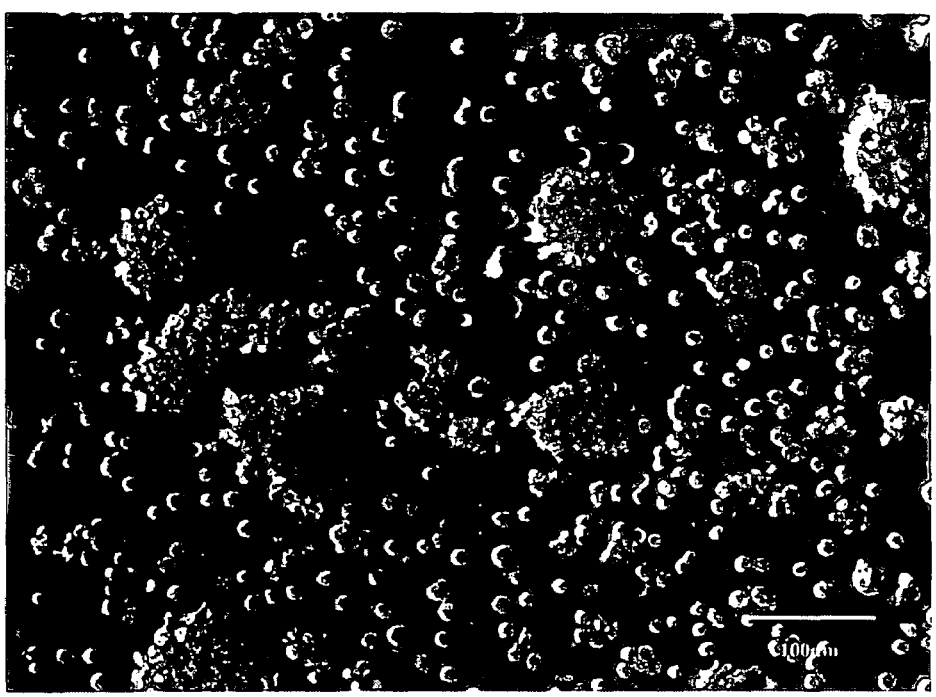
Figure 13:
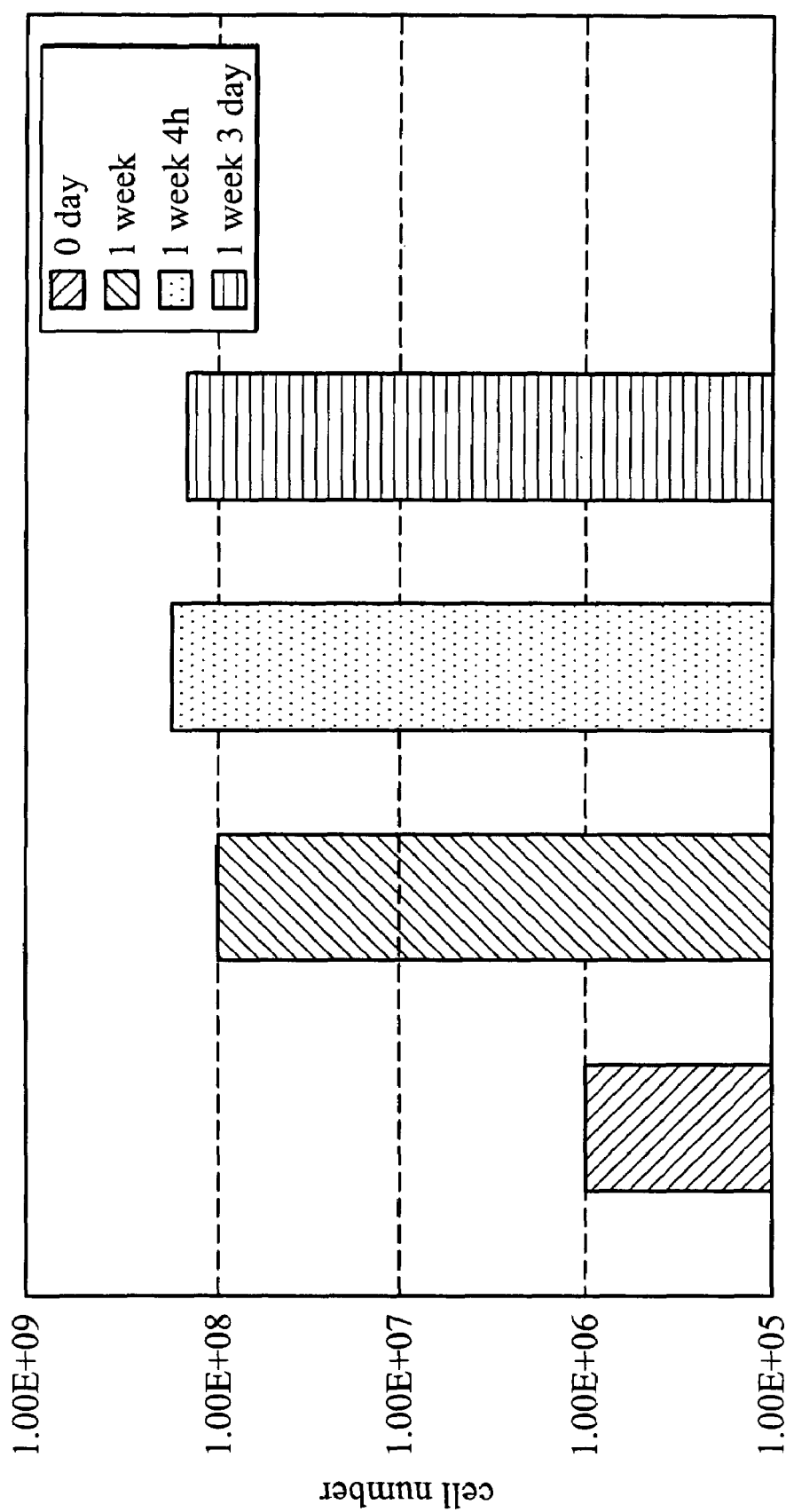
FIG. 13 is a diagram showing L929 cell number changes after culturing in the cell matrix of embodiments of the invention.

Different amplification shows the cells are in a spherical presentation at different sizes as shown in FIGS. 12A and 12B. DNA analysis of L929 cells reveals that the cell matrices of the example of the invention provide sufficient space for L929 cells to grow and proliferate. The proliferation of L929 cells for one week perfusion culturing in the cell matrices is 92 times the original seeding cells.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of producing a porous matrix, comprising:
   providing a plurality of particles containing a multivalent cation;
   adding water to the particles;
   removing excess water from the particles to form a plurality of hydrous particles;
   providing a plurality of the particles containing a multivalent cation in anhydrous form;
   admixing a polysaccharide powder capable of ionic cross-linking with the hydrous particles and the anhydrous particles to form a mixture containing the particles and polysaccharide;
   adding an aqueous solution of a multivalent cation to the mixture to generate cross-linking and form a solidified mixture containing the particles and polysaccharide;
   contacting the solidified mixture with an acid to dissolve the particles in the solidified mixture to form a porous structure; and
   neutralizing the porous structure to obtain the porous matrix, wherein the neutralizing is performed using calcium hydroxide, strontium hydroxide, or barium hydroxide.

2. The method as claimed in claim 1, wherein the particles are at least one hydroxyl-apatite (HAP), tricalcium phosphate (TCP), tetracalcium phosphate ($Ca_4P_2O_9$), $CaHPO_4$, $CaHPO_4.2H_2O$, octacalcium phosphate (OCP), $Ca_2P_2O_7$, calcium carbonate, calcium sulfate, magnesium carbonate, magnesium sulfate, or calcium phosphate.

3. The method as claimed in claim 1, wherein the particles are is between 50~2000 μm in diameter.

4. The method as claimed in claim 1, wherein the polysaccharide powder capable of ionic cross-linking comprises alginate, N,O-carboxymethyl chitosan, or carboxymethyl cellulose.

5. The method as claimed in claim 1, wherein the multivalent cation is provided by calcium chloride, calcium sulfate, calcium carbonate, strontium chloride, strontium sulfate, strontium carbonate, barium chloride, barium sulfate, or barium carbonate.

6. The method as claimed in claim 1, wherein the acid is hydrogen chloride, hypochlorous acid, phosphinic acid, phosphonic acid, phosphoric acid, carbonic acid, acetic acid, or formic acid.

7. The method as claimed in claim 1, further comprising washing the porous matrix after the neutralizing.

8. A porous matrix prepared by the method as claimed in claim 1.

9. The porous matrix as claimed in claim 8, wherein the particles are at least one hydroxyl-apatite (HAP), tricalcium phosphate (TCP), tetracalcium phosphate ($Ca_4P_2O_9$), $CaHPO_4$, $CaHPO_4.2H_2O$, octacalcium phosphate (OCP), $Ca_2P_2O_7$, calcium carbonate, calcium sulfate, magnesium carbonate, magnesium sulfate, or calcium phosphate.

10. The porous matrix as claimed in claim 8, wherein the particles are is between 50~2000 μm in diameter.

11. The porous matrix as claimed in claim 8, wherein the polysaccharide powder capable of ionic cross-linking comprises alginate, N,O-carboxymethyl chitosan, or carboxymethyl cellulose.

12. The porous matrix as claimed in claim 8, wherein the multivalent cation is provided by calcium chloride, calcium sulfate, calcium carbonate, strontium chloride, strontium sulfate, strontium carbonate, barium chloride, barium sulfate, or barium carbonate.

13. The porous matrix as claimed in claim 8, wherein the acid is hydrogen chloride, hypochlorous acid, phosphinic acid, phosphonic acid, phosphoric acid, carbonic acid, acetic acid, or formic acid.

14. The porous matrix as claimed in claim 8, wherein the preparation of the porous matrix further comprises washing the porous matrix after the neutralizing.

15. A method of culturing and recovering cells, comprising:
seeding cells into a solution comprising the porous matrix of claim 8;
culturing the cells on the porous matrix;
dissolving the porous matrix in an ion chelating agent; and
collecting the cells cultured on the porous matrix.

16. The method as claimed in claim 15, wherein the cells are anchorage-dependent.

17. The method as claimed in claim 15, wherein culturing the cells on the porous matrix comprises culturing in a static flat culturing system.

18. The method as claimed in claim 15, wherein culturing the cells on the porous matrix comprises culturing in a dynamic bioreactor cultivating system.

19. The method as claimed in claim 15, wherein the ion chelating agent is EDTA (ethylenediminetetraacetic acid), sodium citrate, or EGTA (ethyleneglycol-bis(2-aminoethylether)-N',N',N',N'-tetraactic acid).

* * * * *